United States Patent [19]
Maxwell, III

[11] Patent Number: 5,299,356
[45] Date of Patent: Apr. 5, 1994

[54] DIET EATING UTENSIL

[76] Inventor: Ralph Maxwell, III, P.O. Box 3028, Hammond, La. 70404

[21] Appl. No.: 44,753

[22] Filed: Apr. 12, 1993

[51] Int. Cl.$^5$ ............... A47J 43/28; H03K 21/18
[52] U.S. Cl. ............................. 30/322; 377/112
[58] Field of Search ............ 30/129, 150, 147, 322; 377/112, 114, 118

[56] References Cited

U.S. PATENT DOCUMENTS

| | | | |
|---|---|---|---|
| 4,513,432 | 4/1985 | Gulati | 377/114 |
| 4,692,640 | 9/1987 | Suzuki et al. | 377/118 |
| 4,833,697 | 5/1989 | Perna et al. | 377/112 |
| 4,993,050 | 2/1991 | Cardemteri et al. | 377/112 |
| 5,075,970 | 12/1991 | Albert | 30/322 |

*Primary Examiner*—Richard K. Seidel
*Assistant Examiner*—Paul M. Heyrana, Sr.
*Attorney, Agent, or Firm*—Keaty & Keaty

[57] ABSTRACT

The invention relates to an eating utensil for counting the number of bites the user consumes in accordance with a specific diet plan regulating the fat intake by the user. The eating utensil has an illuminated display which changes depending on the number of bites consumed by the user. A push button is activated each time the user lifts up a fork full of food from the plate. An associated set of cards carries the names of the food items and the particular number of bites allowed to be taken depending on the fat content of that food item.

12 Claims, 1 Drawing Sheet

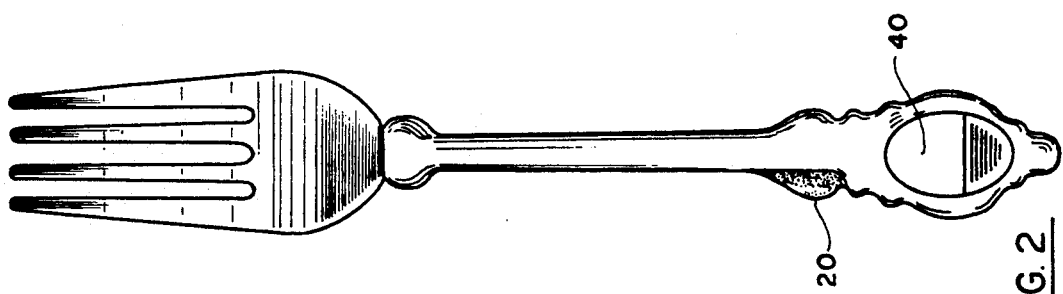
FIG. 3
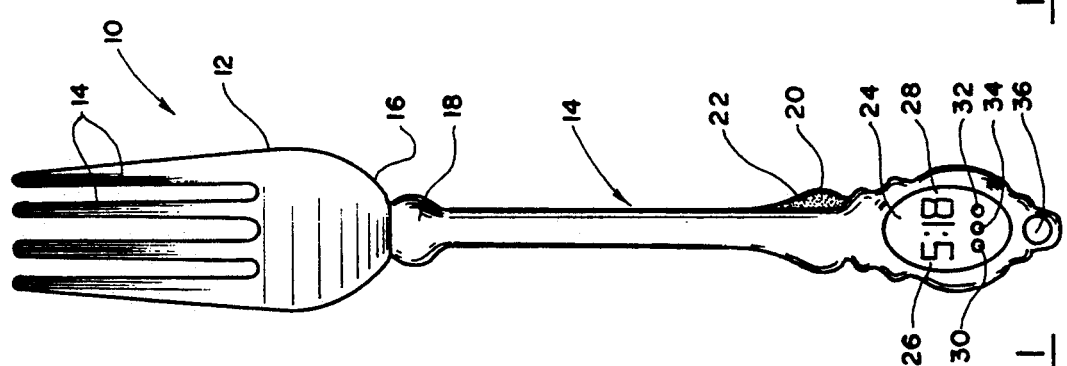
FIG. 2
FIG. 1

DIET EATING UTENSIL

BACKGROUND OF THE INVENTION

This invention relates to eating utensils, and more particularly to an implement which is designed to assist people in controlling the food intake in accordance with a specific diet plan.

In recent years it has been determined that it is the fat content of the foods, more than their caloric intent that should be taken into consideration when following a diet regime.

The top dieters are advised to carefully read the labels of the food they are consuming, to determine the fat content per weight unit and program their diet plan accordingly.

The recent governmental regulations indicate that many packages of food should carry the indicia indicative of fat intake, carbohydrates, sodium, etc content of the food. However, the dieters often eat in restaurants, wherein such information is not available and therefore partake of more fatty foods than is allowed by their diet plan.

The present invention contemplates provision of a eating utensil which will assist dieters in adhering to their diet plan regardless of whether they eat a pre-packaged food or in a restaurant from a plate prepared under the chef's supervision.

SUMMARY OF THE INVENTION

It is therefore a general object of the present invention to provide an eating utensil which displays the amount of bites a person has consumed and which can be correlated to a set of specifically provided cards wherein the maximum amount of the particular food bites is provided.

It is another object of the present invention to provide an eating utensil which provides an alarm means for the eater when the specific amount of bites have been reached.

It is a further object of the present invention to provide a utensil which can display the amount of bites consumed by the dieter, as well as the total amount of bites left depending on the programmed type of food.

It is still a further object of the present invention to provide a set of cooking utensils and dieting charts which list the amount of bites a person is allowed to consume from a specific food group.

These and other objects of the present invention are achieved through a provision of an eating utensil which comprises an implement for conveying the food to the mouth and a handle portion detachably secured to the implement. The handle portion is hollow and encloses an electronic circuit which operates the display means adapted for displaying a total number of bites consumed by the user of a particular type of food. A secondary display means can be provided for displaying the specific number of the bites being consumed in sequence out of the total number of bites which is positioned in association with the first display means. A push button activating means is mounted on the side of the second portion to activate the display means each time the user lifts up a fork full of food from the plate. The hollow handle also carries an independent power source, such as a battery which powers the electronic circuitry inside the handle. An on/off switch mounted in the very tip of the handle allows to activate the circuit and connect it to the battery. The set also includes a number of cards or charts which carry an indicia thereon indicative of the number of bites to be allowed for consumption by the user depending on the fat content of the particular food item. The cards help the user to program the electronic circuit within the eating utensil in accordance with a particular item and any additions such as butter or sour cream added to the food.

BRIEF DESCRIPTION OF THE DRAWINGS

Reference will now be made to the drawings, wherein like parts are designated by like numerals, and wherein FIG. 1 is a front view of an eating utensil in accordance with the present invention.

FIG. 2 is a back view thereof.

FIG. 3 is a front view of a card used for determining the amount of bites allowed in accordance with the diet intake.

DETAILED DESCRIPTION OF THE PREFERRED EMBODIMENT

Referring now to the drawings in more detail, numeral 10 designates the eating utensil in accordance with the present invention which in the drawing is shown to be a fork. It is to be understood, however, that spoons can also be used within the concept of the present invention.

The utensil 10 comprises a first portion 12 having a plurality of tines 14 detachably secured to the second portion or handle 14. The first portion has a narrow inner part 16 which is smaller in width than the inner part 18 of the handle 14, such that the part 16 fitting engages within a hollow body of the handle 14, and specifically within its innermost part 18. Although not shown, securing means, such as a snap spring may be provided within the handle 18 to better secure the first portion 12 to the handle 14.

The handle 14 is substantially hollow and is adapted to house an electronic circuitry therein for providing the necessary counting functions for the dieter. Mounted on the side of the middle portion of the handle 14 is a depressible button 20 which moves between a first position shown in solid lines in FIG. 1 and a second, depressed position shown in phantom lines 22 in FIG. 1. By depressing the button 20 the dieter activates the electrical connection between the counter and the battery, allowing the internal circuity to display the number of bites taken by the dieter.

Mounted in the outermost extreme of the portion 14 is a display means 24 which displays two (2) numbers. The first number 26 designates the particular number of bites taken by the dieter, while the second number 28 designates the total of bites allowed to the dieter based on the particular type of food being consumed. A conventional LED display can be used for the purposes of displaying the numbers through a window in the handle portion 14. A number of buttons 30, 32 and 34 are positioned on the panel on which the display of numbers is provided, the buttons 30, 32 and 34 to program the utensil depending on the type of food the dieter consumes.

Mounted in the tip of the handle portion 14 is an on/off button 36 which operates to activate or deactivate the counting mechanism housed within the handle portion 14.

Turning now to FIG. 2 of the drawings, the handle portion 14 is shown provided with a battery compartment cover 40 which allows access to the battery positioned within the handle portion.

FIG. 3 illustrates a sample chart which is used with the utensil 10 in accordance with the present invention, the chart being designated by numeral 42. As can be seen in the drawing, the chart is divided into a plurality of sections which contain indicia describing different types of foods and the number of bites the dieter is allowed to consume depending on the fat content of the food. As an exemplary indicia box 42 shows "plain potato" inscription, while box 44 displays number 20. By correlating the indicia in boxes 42 and 44, the user will know that he is allowed to consume 20 bites of plain potato.

The next box in the first row, box 46 displays another indicia "with butter" which correlates to the same food item, potato that is displayed in the left hand box of the same row. The next box 48 displays inscription "10" which in combination with the indicia in box 46 will inform the user that only 10 bites of the potato with butter are allowed. In a similar manner, the vertical and horizontal rows of the card 42 are examined by the user, and depending on the number of bites allowed, the user will program the buttons 30, 32 and 34 in order to alert him when the allowed maximum of the food bites has been consumed. For example, before starting the meal, the dieter will program the utensil 10 to display number 18 on the display means 28, indicating that only 18 bites of that particular food are allowed.

The circuitry within the handle portion 14 will automatically display and change the numbers in the display means 26 informing the consumer how many bites out of the allowed 18 he has already consumed. The image displayed on the display means 26 changes with the press of the button 20, which the consumer presses every time he picks up a fork full or a spoon full of food from the plate.

It is envisioned that an alarm means can be provided in the circuitry (not shown) the alarm means sending a slight vibration through the device 10, once the maximum number of bites is reached. Such, once the user consumes 18 bites of the allowed food, and pushes the button 20 for the 19th time, the circuit will activate the vibration means to send the alarm to the user and attract his attention to the consumption of the food over the specified limit.

It is possible to position the button 20 closer to the portion 12, which serves an instrumentality for conveying the food to the mouth of the user, so that the button 20 can be pressed by a forefinger or the users thumb as opposed to the ring finger or the little finger in the embodiment shown in FIG. 1.

It is also possible to eliminate some of the programming buttons 30, 32 and 34 and combine them in one button, depending on the electronic circuitry involved. It is possible to sell the set of eating utensils which contain a fork, a spoon and a salad fork, as well as a booklet containing a dietary plan describing how many points the user gets for "good behavior", when he consumes the fresh fruits and vegetables, as opposed to high fat containing items, such as butter, sauces and the like.

Many other changes and modifications can be made within the design of the present invention without departing from the spirit thereof. I, therefore, pray that my rights to the present invention be limited only by the scope of the appended claims.

I claim:

1. An eating utensil, comprising:
   a first portion for conveying food to the mouth;
   a second substantially hollow portion detachably secured to the first portion, said second portion adapted for engagement by a hand of a user;
   a first display means for displaying a total number of bites allowed to be consumed by the user of a particular type of food item, depending on the fat content of the food item, said first display means being mounted on the second portion;
   a second display means for displaying the specific number of the bites being consumed in sequence of the total number of bites, said second display means being positioned on the second portion; and
   a means for programming the first and second display means mounted on the second portion.

2. The device of claim 1, wherein said programming means comprises means for activating the second display means.

3. The device of claim 2, wherein said activating means comprises a depressible push button located on a side of the second portion and being accessible by a finger of the user.

4. The device of claim 1, further comprising an independent power source for energizing the first and the second display means, and the programming means, said power source being carried by the second portion.

5. The device of claim 1, further comprising an on/off switch carried by the second portion.

6. An eating utensil, comprising:
   a first portion for conveying food to the mouth of the user;
   a second substantially hollow portion detachably secured to the first portion, said second portion adapted for engagement by a hand of the user;
   a display means for displaying the number of bites consumed by the user of a particular food item;
   means for programming the display means mounted on the second portion, for programming the total number of bites allowed to be consumed by the user depending on the fat content of the food item, said programming means being mounted on the second portion;
   depressible means for activating the display means located on a side of the second portion; and
   an on/off switch carried by the second portion.

7. The device of claim 6, further comprising an independent power source for energizing the display means and the programming means, said power source being carried by the second portion.

8. An eating utensil and dietary guide set, comprising;
   an eating utensil for conveying food to the mouth, said utensil comprising a first portion, a second portion detachably secured to the first portion, a display means for displaying a number of bites allowed to be consumed by the user of a particular food item depending on a fat content of that food item, said display means being mounted on the second portion, means for programming the display means mounted on the second portion; and
   a set of charts, each divided into a number of vertical and horizontal rows and having indicia thereon indicating the particular type of food to be consumed and a number of bites to be allowed from the selection of that particular type of food.

9. The assembly of claim 8, wherein said programming means comprises means for activating the display means.

10. The device of claim 9, wherein said activating means comprises a depressible push button located on a side of the second portion.

11. The device of claim 8, further comprising an independent power source for energizing the display means and the programming means, said power source being carried by the second portion.

12. The device of claim 8, further comprising an on/off switch carried by an outer most end of the second portion.

* * * * *